United States Patent [19]

Laforet

[11] 4,164,148

[45] Aug. 14, 1979

[54] METHOD FOR DETERMINING SULFUR CONTENT OF CAST IRON

[76] Inventor: Henry A. Laforet, 3903 Scenic Dr., North Muskegon, Mich. 49445

[21] Appl. No.: 901,370

[22] Filed: May 1, 1978

[51] Int. Cl.$^2$ ............................................. G01N 33/20
[52] U.S. Cl. .................................. 73/432 R; 73/17 R
[58] Field of Search ................... 73/432 R, 17 R, 354, 73/DIG. 9

[56] References Cited

U.S. PATENT DOCUMENTS

| | | | |
|---|---|---|---|
| 3,375,106 | 3/1968 | McKissick et al. | 73/17 R |
| 3,670,558 | 6/1972 | Ryntz, Jr. et al. | 73/17 R |

FOREIGN PATENT DOCUMENTS 2403146  9/1974  Fed. Rep. of Germany .......... 73/17 R

OTHER PUBLICATIONS

*Carbon Equivalent in 60 Seconds*, in Modern Castings, pp. 37–38, Mar. 1962.

*Primary Examiner*—S. Clement Swisher
*Assistant Examiner*—Joseph W. Roskos
*Attorney, Agent, or Firm*—Irons & Sears

[57] ABSTRACT

A test for determining the sulfur content of the base cast iron used for the production of nodular iron or iron containing compacted graphite. A sample of the molten base cast iron is removed from the melt, then a known amount of a nodular iron inoculant or a compacted iron inoculant is added to the molten metal. The molten metal sample is then cast into test bar or test wedge, solidified and tested to determine whether the bar or wedge is nodular iron or iron containing compacted graphite. The test may be fractured and inspected to visually determine whether the fracture is gray or white. Alternatively, the wedge or bar may be ultrasonically tested to determine whether the wedge or bar contains flake graphite or nodular graphite or compacted graphite. As a further alternative, the cooling or solidification curve of the molten metal sample, after inoculation, can be determined and compared with the cooling curve from a molten base cast iron sample. The comparison will show the shifting of the phase change points between the two curves, and this shifting can be correlated with the sulfur content of the base cast iron to form the basis for determining the amount of nodularizing inoculant to be added to the base metal, thus insuring adequate, yet not wasteful, inoculant addition during production. The inoculant can be added by various procedures and, by performing certain initial, qualifying tests, the sulfur content of any base metal composition can be determined with accuracy and without the need for either chemical or spectroscopic analysis.

9 Claims, 10 Drawing Figures

METHOD FOR DETERMINING SULFUR CONTENT OF CAST IRON

BACKGROUND OF THE INVENTION

Grey cast iron contains carbon in the form of "flakes" and has low tensile strength and a low modulus of elasticity, but relatively high thermal conductivity. Nodular irons or ductile irons contain carbon in the form of "nodules" or "spheroids". Nodular iron has higher strength and good ductility, but lower thermal conductivity. Compacted graphite irons contain graphite in the form of flakes having rounded ends and generally the flakes are short and thick. Actually, compacted graphite iron is intermediate nodular iron and grey iron and has generally intermediate properties. The strength and ductility of compacted graphite iron approaches that of ductile, yet the thermal conductivity is nearer to that of grey iron.

In both ductile iron and compacted graphite iron, the modified graphitic structure is produced by the inoculation of essentially white cast iron compositions with a "nodularizing inoculant". Commercially, the "nodularizing inoculants" are magnesium or cerium or a mixture of the two. Other known nodularizing inoculants include calcium, lithium, sodium, barium, and the rare earth metals. In the case of compacted graphitic iron, titanium is usually added to inhibit nodularization and to insure the presence of the graphite in the compacted form; rather than in the nodular form. See the article by K. B. Palmer in British Cast Iron Research Association Journal, January, 1976, at pages 31-37.

Typical base metal compositions for the manufacture of nodular iron has the following composition:
  Total Carbon: 3.20-4.10 percent by weight
  Silica: 1.5-2.80 percent by weight
  Manganese: Up to 0.80 percent by weight
  Phosphorus: 0.10 maximum percent by weight
  Sulfur: 0.03 maximum percent by weight
  Iron: Balance The criticality of the sulfur content of the base iron has long been recognized. To obtain the maximum mechanical properties in sound nodular iron castings or sound compacted graphite castings, the sulfur content of the base iron composition should be less than about 0.03% at the time of inoculation. To retain the sulfur content at such a low level, extreme control measures have been taken. The sulfur can be controlled by using base materials or ingredients which are low in sulfur, or by desulfurizing the melt or by a combination of both.

Excessive sulfur in the base metal melt preferentially reacts with the magnesium or other nodular inoculant, and insufficient residual inoculant remains to perform its nodularizing or compacting function. Further, the presence of excess inoculant is harmful, since it results in inferior types of microstructures, the final nodular iron is more prone to carbidic structures, the inoculant itself is wasted, and attempts at obtaining a compacted graphite structure may result in an undesired nodular structure.

All in all, it will be readily appreciated that the control of sulfur is of extreme importance in the manufacture of either nodular iron or compacted graphitic iron and knowledge of the precise sulfur content is critical for efficient, metallurgically sound operation. Previously, the sulfur content has been determined by chemical analysis, by microstructure observation or by spectographic analysis. Each such test is time consuming and requires holding the base metal at pouring temperature while the test is performed, and each form of tests requires equipment and facilities which are not present in many foundries.

The only other test normally utilized is the visual fracture inspection performed on test pins poured from the iron composition after inoculation has been completed. Obviously, this test tells whether or not one has nodular iron or iron containing compacted graphite, but it does not reflect the character of the base metal itself, and it does not prevent the pouring of bad castings. The pouring of test pins prior to pouring the casting requires holding the inoculated molten metal during pouring and breaking of the test pins.

The problem of accurately determining the sulfur content is even more acute where the primary inoculant is added by the in-mold process, e.g. as proposed in U.S. Pat. Nos. 3,746,078 or 3,765,876. Here, the sulfur content must be known before pouring of the metal into the mold, since it is impossible to test the effectiveness of the inoculant prior to pouring.

BRIEF DESCRIPTION OF THE PRESENT INVENTION

The present invention now proposes a novel test for the basic molten metal to be used in the manufacture of nodular iron or compacted graphitic iron to determine the sulfur content within a relatively narrow range and without the performance of complicated laboratory tests which require extended periods of time and extensive laboratory facilities.

More specifically, the present invention proposes the addition to the molten sample of the base metal of a nodularizing inoculant, such a cerium or magnesium, solidifying the inoculated sample into a test bar or wedge and then alternatively (1) visually determining the character of a fractured portion of the sample or (2) ultrasonically determining the modification of the carbon content to either nodular or compacted graphite or (3) comparing solidification curves obtained during cooling of a base metal sample and the inoculated sample. Expressed in another manner, the method of the present invention determines the amount of nodularizing inoculant necessary to eliminate flake, non-nodular or non-compacted, carbon from the sample and then adds this amount to later, periodic samples to determine any deviation in the sulfur content of the sample.

The amount of cerium added to the molten metal sample is known, and the extent of nodularization or compaction can be determined by visual inspection of the sample following solidification. From these two pieces of knowledge, the amount of sulfur in the base metal can be determined.

The nodularizing ingredient can be added in any desired fashion, so long as (1) a known weight percent of ingredient is added to the base metal sample, and (2) the ingredient is thoroughly and completely dispersed in the sample. One manner of addition is by incorporating the ingredient, such as cerium, with fillers, such as clay, and binders, such as pitch, into a pellet containing a predetermined amount of nodularizing ingredient.

Such pellets can be incorporated into the sample by simply placing them in a sample ladle prior to filling the ladle or by placing them in the flow path of the sample into the ladle or into the test bar or wedge mold, or by stirring them into an already filled ladle or mold, or by any other desired method.

Essentially, the visual test of the present invention relies upon the fact that chilled, properly nodularized or compacted iron exhibits a white fracture, as compared with the gray fracture of chilled iron in which the nodularizing agent is ineffective due to excessive sulfur. Upon breaking of the sample, the coloration of the fracture is observed. If the fracture is white, the amount of sulfur in the sample is less than that which would neutralize the added amount of nodularizing agent. Further, where the fracture is performed on a test bar or wedge of polygonal cross-section and having corners of differing angularity, e.g. a 30°-60°-90°-triangular shape, the severity of the chill—and the occurrence of white fracture—varies from corner to corner. By noting which and how many corners are white, the amount of sulfur in the base metal can be determined with accuracy, i.e. a 30° wedge angle chills more quickly than either a 60° or 90° wedge angle and will exhibit a white fracture at higher sulfur contents. Thus, a sample wherein all three angles fracture white contains less sulfur than a sample wherein only the 30° angle exhibits a white fracture.

Alternatively, the test bar or wedge can be ultrasonically tested by commercially available apparatus manufactured by Magnaflux Corporation to determine the extent to which flake graphite has been eliminated.

Another testing technique is to determine the cooling curves of a sample of base cast iron and an inoculated sample, compare the curves and then correlate the comparison with the sulfur content of the base cast iron. Both Electro-nite Company of Philadelphia, Pa. and Leeds & Northrup Company of North Wales, Pa. make apparatus for determining such cooling or solidification curves. The presence of other impurities or undesirable metal constituents in the base metal and their effect upon the test procedure can be determined by the running of a series of initial qualifying tests on the base metal, wherein graduated amounts of cerium and/or other nodularizing ingredient are added to the base metal sample and the appearance of the test bar or wedge is observed. Once such a qaulifying test has been run, individual test bars or wedges can be utilized to determine the amount of sulfur in each successive ladle or pour extracted from the cupola or other source of molten cast iron. The qualifying tests need only be run when basic or massive changes are made in the source of molten metal, i.e. when initially tapping a fresh cupola charge; or at predetermined, scheduled intervals, i.e. at each shift change.

After the qualifying series of tests have been run, the test preferably is performed for each ladle or pour of molten metal prior to the inoculation with the primary inoculant. Alternatively, the test may be performed on a regular schedule, e.g. alternate pours, every third pour, etc. A molten sample is withdrawn, the test inoculation is made by any of the techniques above described, the test bars or wedges are poured, solidified and fractured or ultrasonically tested. By observing the location, extent and character of the whitened portions of the fractured bar or wedge, and by comparison with the qualifying series if desired, the sulfur content of the sample can be determined visually.

The test results are then utilized to determine the amount of primary inoculant which must be added to the molten metal to obtain nodularization or compaction within the narrow limits necessary to prevent over-inoculation or under-inoculation.

ON THE DRAWINGS

DETAILED DESCRIPTION OF THE PREFERRED EMBODIMENTS

Figure 1:
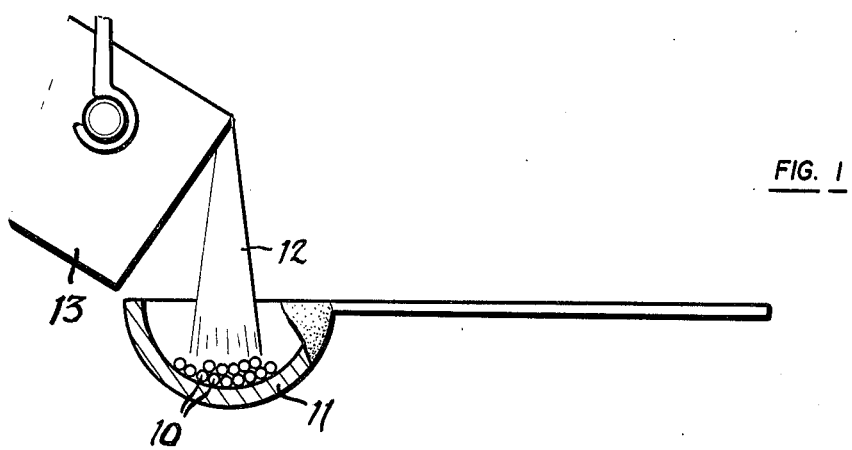
FIG. 1 is a schematic view of a ladle receiving molten cast iron from the cupola or the like and containing inoculant pellets of the present invention.

As herein before explained, the percentage of sulfur present in the base cast iron from which either nodular iron or compacted graphite iron castings are to be made is of extreme importance. A typical base metal composition for making nodular iron falls within the following analysis:

| COMPOSITION | PERCENT BY WEIGHT |
|---|---|
| Total Carbon | 3.20–4.10 |
| Silica | 1.5–2.80 |
| Manganese | Up to 0.80 |
| Phosphorus | 0.10 maximum |
| Sulfur | 0.03 maximum |
| Iron | Balance |

Other ingredients are kept to a minimum, since they inhibit the formation of carbon nodules or the compaction of the carbon. Such ingredients include lead, bismuth, antimony, and tin.

In the manufacture of nodular iron, an addition of a nodularizing inoculant is made to the base iron immediately before or during pouring of the casting. Generally, an addition of magnesium or cerium is utilized, often as an alloy with ferrosilicon. The amount of innoculant addition is calculated to leave a residual magnesium content in the final casting of less than about 0.08%. All of this technology is quite known and is in common use today.

In the manufacture of compacted graphite irons, similar base compositions are utilized, a typical base iron having a nominal composition of 3.7% carbon, 1.7% silican, 0.3% manganese and less than 0.03% sulfur being typical. By the addition of magnesium in an amount to produce from 0.015% to 0.020% residual magnesium content, a compacted graphite structure can be obtained. Magnesium contents greater than 0.020% generally produce substantially nodular graphite structures, while final compositions containing less than 0.015% residual magnesium yields a flake graphite structure. By the addition of titanium in an amount ranging generally from about 0.06% to about 0.13%.

compacted graphite structures can be obtained with residual magnesium contents ranging from about 0.015% to 0.030%. It has been found that the addition of cerium in extremely minute amounts promotes the formation of compacted graphite. One successful process utilizes an inoculant which is an alloy having a ferrosilicon base and containing 5% magnesium, 7% titanium and 0.3% cerium has been successful, the alloy being added in an amount ranging from about 0.75% to about 1% by weight of the base metal.

The sulfur content of the base metal is of extreme importance, the sulfur acting as an inhibitor to the formation of the compacted graphite, so that normal inoculant additions to base irons of high sulfur content would yield a final composition containing flake graphite.

For all of these reasons, it is quite necessary to have knowledge of the sulfur content of the base metal. Previously utilized procedures, including chemical analysis for sulfur or the pourings of testings after inoculation, are unsatisfactory for the reasons herein before given in detail.

The method of the present invention proposes the addition of a nodularizing or compacting inoculant to a sample of the base metal, forming a frangible test piece from the inoculated sample, fracturing the test piece and observing the appearance of the fracture.

The inoculant can be anyone of several nodularizing ingredients, typically magnesium or cerium. Preferably, the nodularizing ingredient is utilized in a solid form or as a solution containing a known amount of the active inoculation ingredient. For example, cerium or magnesium can be incorporated into a pellet along with chemically inert pelletizing ingredients, such as clay and pitch. Each pellet contains a predetermined amount of magnesium or cerium, so that the pellets merely need be counted out to insure a known quantity of active ingredient for a known weight of test sample. If a one pound sample were to be taken, and 0.25% cerium is to be added, one pellet containing 0.0025% lbs. of cerium would be added to the sample. If it were desired to add 0.50% cerium, then two pellets would be added to a one pound sample.

Alternatively, the known amount of cerium maybe incorporated by soaking a strainer in a cerium solution until a known amount of cerium has been absorbed by the strainer. A mold wash containing cerium also could be utilized. Again, another alternative would be the suspension of a known weight of cerium in a stream of air or carbon dioxide under pressure and blowing the air or carbon dioxide through the sample of the base metal.

In any event, a known weight of cerium is added to the molten base metal. The inoculated base metal is then formed into a test wedge or bar which is fractured and the plane of fracture is observed. If the fracture is white, the base metal has been converted to nodular iron or compacted graphitic iron by the amount of cerium or magnesium which has been added. Therefore, the sulfur level is below that which yields a residual cerium or magnesium content retained in the inoculated casting in amount sufficient to obtain nodular or compacted graphite.

Specific methods are illustrated in the attached drawings. In FIG. 1, the simplest form of addition has been made. The requisite number of inoculant pellets 10 have been placed in the ladle 11 and molten metal 12 is introduced into the ladle from the cupola or other supply of molten metal 13. The molten metal 12 disolves the pellets 10 so that the inoculation is effected. If necessary, the metal-pellet mixture may be stirred with a refractory stirring rod to insure disbursion of the pellets throughout the molten metal.

Figure 2:
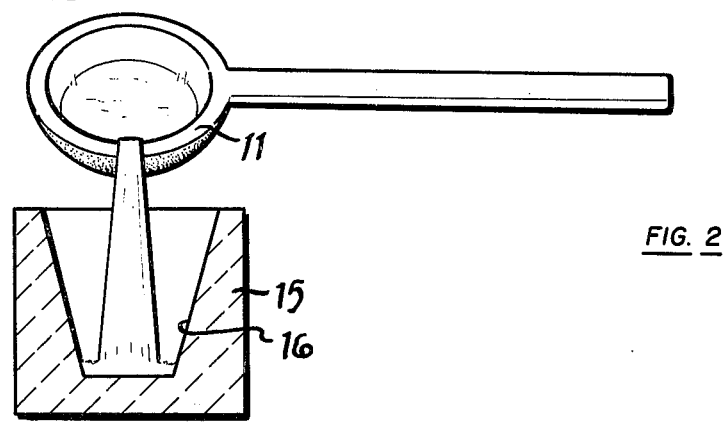
FIG. 2 is a schematic view illustrating the pouring of the triangular wedge sample from the ladle of FIG. 1.

Next, as illustrated in FIG. 2, the inoculated metal is poured from the ladle 11 into a sand wedge mold 15 having an interior cavity 16 defending the shape of the test wedge.

Figure 3:
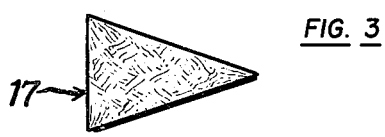
FIG. 3 is an elevational view of the fracture plane of a test wedge of nodular iron or compacted graphitic iron.
Figure 4:
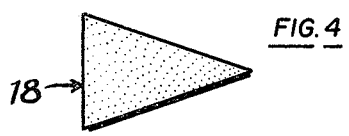
FIG. 4 is a view similar to FIG. 3, but illustrating a test wedge of grey iron.

After solidification within the mold cavity 16, the test wedge is removed and fractured. If the fracture of the test wedge 17 is all white, as indicated in FIG. 3 of the drawings, then the inoculated metal is capable of forming modular iron and the sulfur content of the base metal is less than that which would yield nodular iron upon the addition of an inoculant corresponding to the amount of cerium which has been added. If the fracture is grey or mottled, as in the wedge 18 of FIG. 4, then the inoculation has not been successful and the sulfur content is greater.

For example, it is known that for the production of nodular iron or compacted graphite from a base metal innoculated with 0.25% cerium, the sulfur content is less than 0.008% by weight. Similarly, the production of white iron from a base metal containing 0.50% cerium means that the base metal contains less than 0.016% sulfur.

This data is presented in tabulated form in Table 1 represents the fracture characteristics of a typical base cast iron when inoculated with the indicated amount of cerium.

TABLE I

| Cerium Added (% by weight) | | | | |
|---|---|---|---|---|
| 0.25 | 0.50 | 0.75 | 1.0 | Sulfur in base metal (% by weight) |
| Appearance of Test Bar Fracture | | | | |
| White | White | White | White | 0.008 |
| Mottled | White | White | White | 0.008 0.016 |
| Mottled | Mottled | White | White | 0.016 0.024 |
| Mottled | Mottled | Mottled | White | 0.024 0.036 |
| Mottled | Mottled | Mottled | Mottled | 0.036 |

Figure 5:
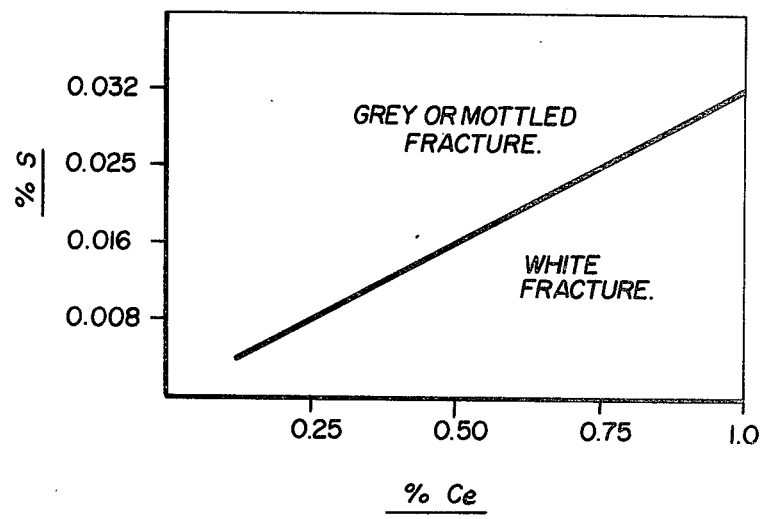
FIG. 5 is a graphic representation in which the percentage of cerium added to the sample is plotted against the percent sulfur in the sample, and the appearance of the test wedge fracture is plotted thereon.

This same data is presented graphically in FIG. 5 of the drawings.

Of course, the tabulated data of Table 1 and graphic data of FIG. 5 will vary with the base metal composition and with the section size. Preferably, the overall base metal composition is chemically determined with some accuracy, then a given weight of molten base metal is treated with varying amounts of cerium and then fractured to derive a table similar to Table 1 or a graph similar to FIG. 5 for that specific base metal composition. So long as the same general or overall base metal composition and the same section size of fractured sample is retained, the graphic representations of Table 1 and FIG. 5 remain true and provide the basis for subsequent individual tests.

Once the tabular material and the graph have been generated for a given overall base metal composition, the amount of primary inoculant to be added is calculated from the known sulfur content. Molten base metal samples are then withdrawn at regular intervals, preferably prior to each pour or ladle withdrawn from the cupola, the test of the present invention is performed to determine that the sulfur content has not changed, and the castings are then poured using the known amount of inoculant. In the event that the test indicates a deviation from the sulfur content appropriate to the planned inoculant, then the amount of inoculant is adjusted to insure that neither too little nor too much inoculant is added.

Figure 6:
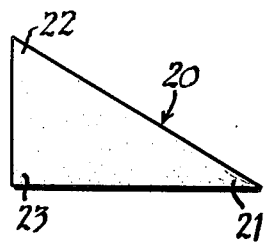
FIGS. 6, 7 and 8 illustrate the appearance of test wedges from molten metal containing various amounts of sulfur.
Figure 7:
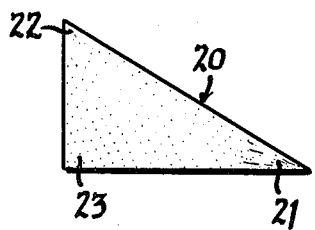
Figure 8:
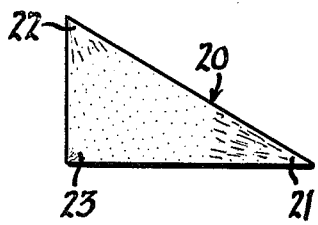

An even more sensitive tests is illustrated by the test bar fractures shown in FIGS. 6, 7 and 8. Here, the test bar is in the form of a 90°, 60°, 30° triangle. The 30° angle chills more quickly and to a greater extent than the 60° angle 22, and the 60° angle 22 chills more quickly than the right angle 23. For a typical base metal analysis, the formation of white iron only in the angle A would indicate a sulfur content of greater than 0.015% in the base metal. This is the condition illustrated in FIG. 5. If the chill is as indicated in FIG. 6, both the angles 21 and 22 are white and the sulfur content is between 0.10% and 0.015% in the base metal. If the chill is in angles 21, 22 and 23, as illustrated in FIG. 7, then the sulfur content of the base metal is below 0.10%. Once again, it is necessary to run a chemical analysis of the initial base metal and then to correlate the base metal with the appearance of whitening at the angles 21, 22 or 23 in order to determine the sulfur content for any given base metal composition.

Figure 9:
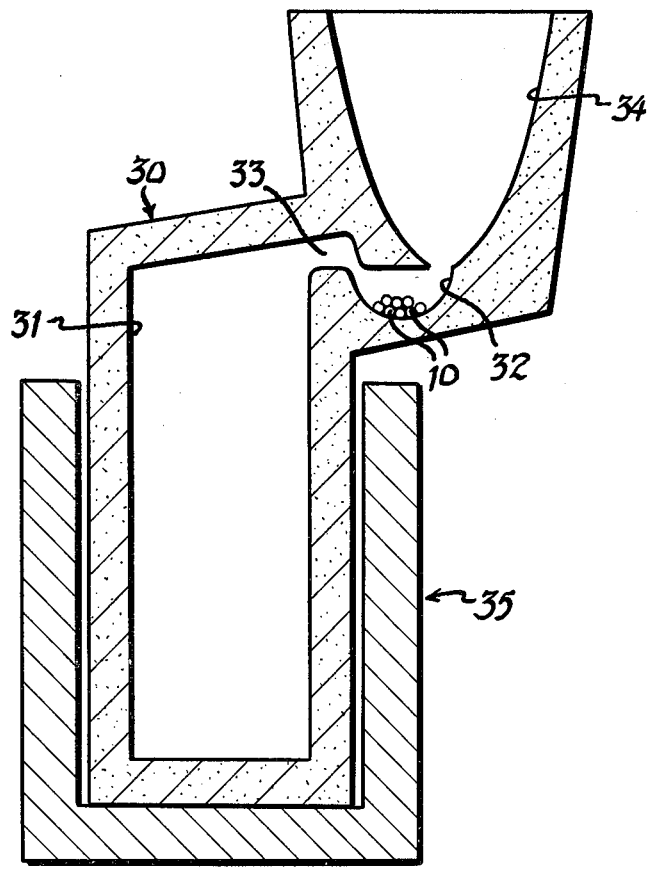
FIG. 9 is a schematic sectional view of the different form of test wedge mold.

A different method of innoculant addition is shown in FIG. 9 of the drawings. Here, the sample mold 30 includes a preferably triangular test wedge cavity 31 connected with a reservoir 32 through a filling restriction 33, the reservoir freely communicating with an upper receiving chamber 34. The entire mold 30 is retained in an upright position by a metal holder 35. Molten base metal is poured into the receiving section 39 and flows through the reservoir 32 in which pellets 10 have been placed. Flow from the reservoir is restricted by the opening 33, so that the flowing metal disolves the pellets into the base metal. Thus, the base metal is innoculated by the pellets prior to its entry into the mold cavity 31.

Upon solitification of the test wedge in the cavity 31, the mold is broken open, the sample wedge is removed and fractured as above described.

Figure 10:
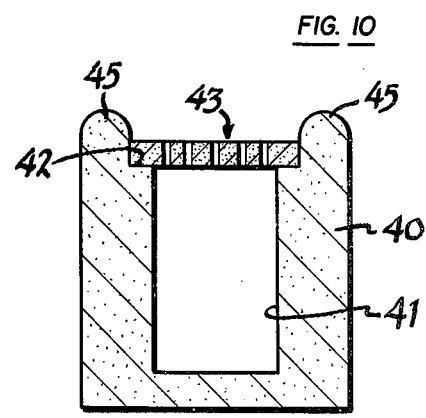
FIG. 10 is a schematic sectional view of yet another form of test wedge mold.

Another, different form of innoculation utilizes the apparatus illustrated in FIG. 10 of the drawings. Here, a sand mold 40 surrounds an interior mold cavity 41, preferably of wedge shape. Mold 40 is provided with an annular supporting flange 42 upon which a perforate strainer 43 is seated. The mold walls extend upwardly, as at 45, to provide a reservoir for molten metal overlying the strainer 43. The strainer 43 is preferably formed of sand reinforced with resin, as is well known in the prior art, and is either impregnated with cerium, or contains cerium admixed therewith, or is coated with a cerium wash. Molten metal poured into the reservoir above the strainer 43 then flows through the strainer into the mold cavity 41. As it passes over and through the strainer, the cerium incorporated into the strainer or coated onto the strainer will be disolved by the molten metal so that the metal becomes inoculated with the cerium.

The strainer 43 can be made in different categories containing different amounts of cerium to be dissolved out by the molten metal flowing there through. For example, the strainer may inoculate the molten metal with graduated amounts of cerium ranging from 0.25% to 1.0% cerium for the weight of the test bar. The porous sand strainer can be soaked in a solution of cerium for varying period of time, so that varying amounts of cerium are impregnated into the strainer.

Other methods of inoculation maybe utilized. The pellets 10 may be placed on a strainer as illustrated in FIG. 10, or the pellets may simply be dropped into a ladle or a mold into which the molten base metal is directly poured. The mold walls themselves maybe coated with a cerium or magnesium bearing solution, paste or slurry, or the ladle maybe coated with such a solution or suspension, or powdered or palletized innoculant maybe blown into the ladle or into the mold in a stream of inert gas.

Further, while the above discussion of the method has been concerned with triangular or wedge-shaped test bars, there is no reason that the test bar could not be cylindrical in shape or in the shape of any desired polygon in cross section.

An alternative testing method depends upon the difference in the transition of ultrasonic vibrations by grey cast iron, nodular cast iron and cast iron containing compacted graphite. These differences can be determined by measuring the time required for the transition of ultrasonic vibrations thru equal lengths of test bars from the base cast iron and the inoculated cast iron.

A third alternative involves the shift in the phase transition points of a solidification curve, which shift occurs when the base cast iron is inoculated with a nodularizing ingredient. The test curves are derived during the solidification of molten base cast iron and inoculated cast iron samples by the utilization of commercially available apparatus, the curves are compared on the basis of the location of the phase shift points, and the comparison is correlated with the amount of sulfur in the base cast iron. The amount of primary inoculant, e.g. magnesium, magnesium-cerium mixture, etc., necessary to convert the base coast iron to either nodular or compacted graphite iron can be readily calculated.

In summary, it will be seen that the present invention provides a quick, definite, visual test for the sulfur content of cast irons, and the physical samples of the cast iron can be marked and retained for a permanent record. Once the initial screening has been accomplished, no further complicated, time-consuming, skilled chemical testing is required and the tests results correlate directly with the inoculation capability of the base metal.

I claim:
1. The method of determining the sulfur content of cast iron by the steps of
   (1) adding to a sample of molten cast iron iron an amount of cerium ranging from 0.25% to about 1.0% by weight of the sample,
   (2) casting the sample into a test bar having a cross section in the form of a 60°, 30°, right triangle,
   (3) fracturing the test bar,
   (4) observing the location and amount of any white areas in the test bar to determine the sulfur content of the metal constituting the test bar.

2. The method of determining the sulfur content of a base cast iron, comprising the steps of
   (1) pouring a molten sample of the base cast iron into a test bar;
   (2) during the performance of Step (1) incorporating into the molten metal an amount of a nodular iron innoculant sufficient to convert the cast iron to nodular iron if the sulfur content of the test bar is less than about 0.03% by weight; and
   (3) visually or ultrasonically determining whether the test bar is nodular iron.

3. The method of determining the sulfur content of a base cast iron, comprising the steps of
   (1) pouring a sample of the molten base metal through a flow path into a test bar mold;

(2) interposing in said flow path a source of nodular iron inoculant;

(3) during the performance of Steps (1) and (2), incorporating the inoculant into the molten base metal; and (4) determining whether the innoculant has reacted with the sulfur content of the base metal and the test bar is free of flake graphite.

4. The method of determining the sulfur content of molten cast iron, comprising the steps of (1) removing a sample of the molten cast iron;

(2) forming the molten cast iron sample into a test wedge;

(3) during the performance of Steps (1) and (2) incorporating into the molten sample a known amount of a nodularizing inoculant;

(4) fracturing the sample test wedge; and (5) observing the coloration of the test wedge at the point of fracture to determine whether the inoculant has reacted with all the sulfur in the samples and has converted the test metal into nodular iron or compacted graphic iron.

5. The method of determining the sulfur content of a molten base cast iron preparatory to the inoculation of the cast iron to form either nodular iron or compacted graphite iron, comprising the steps of (1) withdrawing a molten sample of the base cast iron;

(2) solidifying the molten sample into a test wedge;

(3) intermediate Steps (1) and (2) incorporating a known amount of an inoculant selected from the group consisting of cerium and magnesium into the molten base cast iron; and (4) determining whether the test bar is free of residual sulfur and flake carbon.

6. The method of determining the sulfur content of molten cast iron comprising the steps of (1) inoculating a series of molten samples of the molten cast iron with varying amounts of an innoculant selected from the group consisting of cerium and magnesium, (2) testing each sample to determine the amount of inoculant necessary to eliminate flake carbon from the sample, (3) comparing the necessary amount determined in Step (2) with a chemical analysis of the cast iron sulfur content, and (4) thereafter inoculating periodic samples with said inoculant in the necessary amount to determine any variation of the sulfur content of such periodic samples.

7. The method of determining the sulfur content of molten cast iron comprising the steps of (1) withdrawing two molten samples of the base cast iron;

(2) inoculating one sample with a known amount of a nodularizing ingredient;

(3) solidifying each sample;

(4) during the performance of step (3) measuring the solidification curve of each sample; and (5) comparing the shift change points of the two curves determine whether the known amount of nodularizing ingredient has eliminated sulfur and flake graphite from the inoculated sample.

8. The method of determining the sulfur content of molten cast iron comprising the steps of (1) withdrawing two molten samples of the base cast iron;

(2) inoculating one sample with a known amount of a nodularizing ingredient;

(3) solidifying each sample;

(4) transmitting ultrasonic vibrations through each sample;

(5) during the performance of step (4) measuring the time of transmission; and (6) comparing the transmission times to determine whether the known amount of nodularizing ingredient has eliminated sulfur and flake graphite from the inoculated sample.

9. The method of determining the sulfur content of a molten base cast iron preparatory to the inoculation of the cast iron to form either nodular iron or compacted graphite iron, comprising the steps of (1) withdrawing a molten sample of the base cast iron;

(2) solidifying the molten sample into a test wedge;

(3) intermediate Steps (1) and (2), blowing into the molten iron an inert gas having suspended therein a known amount of an inoculant selected from the group consisting of cerium and magnesium; and (4) determining whether the test bar is free of residual sulfur and flake carbon.

* * * * *